United States Patent [19]
Cohn et al.

[11] Patent Number: 5,076,696
[45] Date of Patent: Dec. 31, 1991

[54] DYNAMIC IMAGING MICROELLIPSOMETRY

[75] Inventors: Ralph F. Cohn, Worcester, Mass.; James W. Wagner, Annapolis, Md.

[73] Assignee: The Johns Hopkins University, Baltimore, Md.

[21] Appl. No.: 324,494

[22] Filed: Mar. 16, 1989

[51] Int. Cl.$^5$ .......................... G01N 21/21; G01J 4/04
[52] U.S. Cl. ..................................... 356/369; 250/225
[58] Field of Search .......................... 356/369; 250/225

[56] References Cited

U.S. PATENT DOCUMENTS 4,516,855  5/1985  Korth .............................. 356/369 X

OTHER PUBLICATIONS

Cohn, Wagner, and Kruger, "Dynamic Imaging Microellipsometry: Theory, System Design and Feasibility Demonstration", *Applied Optics*, vol. 27, No. 22, pp. 4664–4671, Nov. 1988.
Kruger et al., "Qualitative Use of Ellipsometry to Study Localized Corrosion Processes", *Surface Sci.*, vol. 56, No. 1, pp. 394–412, Jun. 1976.
Mishima et al., "Determination of Spatial Distributions of Thickness . . . ", *Applied Optics*, vol. 20, No. 21, pp. 3719–3722, Nov. 1981.
Ralph F. Cohn, "Dynamic Imaging Microellipsometry", Journal of the Electrochemical Society, Apr. 1988, pp. 1033 and 1034.
J. Kruger, "Application of Ellipsometry to Electrochemistry", pp. 226–280.
C. L. McBee and J. Kruger, "Events Leading to the Initiation of the Pitting of Iron", pp. 252–260.
Carol Lee McBee and Jerome Kruger, "Ellipsometric-Spectroscopy of Films Formed on Metals in Solution", Surface Science 16 (1969) 340–352, pp. 340–353.
Katsuhisa Sugimoto and Shiro Matsuda, "Analysis of Passive Films on Austeno-Ferritic Stainless Steel by Microscopic Ellipsometry", J. Electrochem. Soc: Electrochemical Science & Technology 12/1983, vol. 130, No. 12, pp. 2323-2328.
K. Sugimoto, S. Matsuda, Y. Ogiwara, K. Kitamura, "Microscopic Ellipsometric Observation of the Change in Passive Film on 18Cr-8Ni Stainless Steel with the Initiation and Growth of Pit", Electrochemical Science and Technology, vol. 132, No. 8, pp. 1791-1795.
Rolf II. Muller, "Principles of Ellipsometry", pp. 167-227.
M. Erman and J. B. Theeten, "Spatially Resolved Ellipsometry", J. Appl. Phys. 60(3), Aug. 1, 1986, pp. 859-873.
D. J. Dunlavy, R. B. Hammond, R. K. Ahrenkiel, "A Scanning Microellipsometer for the Spatial Characterization of Thin Films".
"Auto Gain Ellipsometers", Gaertner Scientific Corporation, Bulletin EE, pp. 1-21.
Alan J. Hurd and C. Jeffrey Brinker, "Optical Sol-Gel Coatings: Ellipsometry of Film Formation", J. Phys. France 49 (1988).
Alan J. Hurd and C. Jeffrey Brinker, "Ellipsometric Imaging of Drying Sol-Gel Films".

*Primary Examiner*—Davis L. Willis
*Assistant Examiner*—Matthew W. Koren
*Attorney, Agent, or Firm*—Cushman, Darby & Cushman

[57] ABSTRACT

Dynamic imaging microellipsometry (DIM) is a rapid full-field imaging technique for high resolution studies of thin-films. The DIM concept is based on radiometric polarizer, compensator, specimen, analyzer (PCSA) ellipsometry combined with video and image processing techniques. The theoretical basis for this approach is developed using the Jones vector and matrix formalism. Basic systems design is presented with error model predictions of ellipsometric accuracies better than 0.1° for full-field $\psi$ and $\Delta$ images captured in a few seconds with spatial resolution under 10 microns.

15 Claims, 4 Drawing Sheets

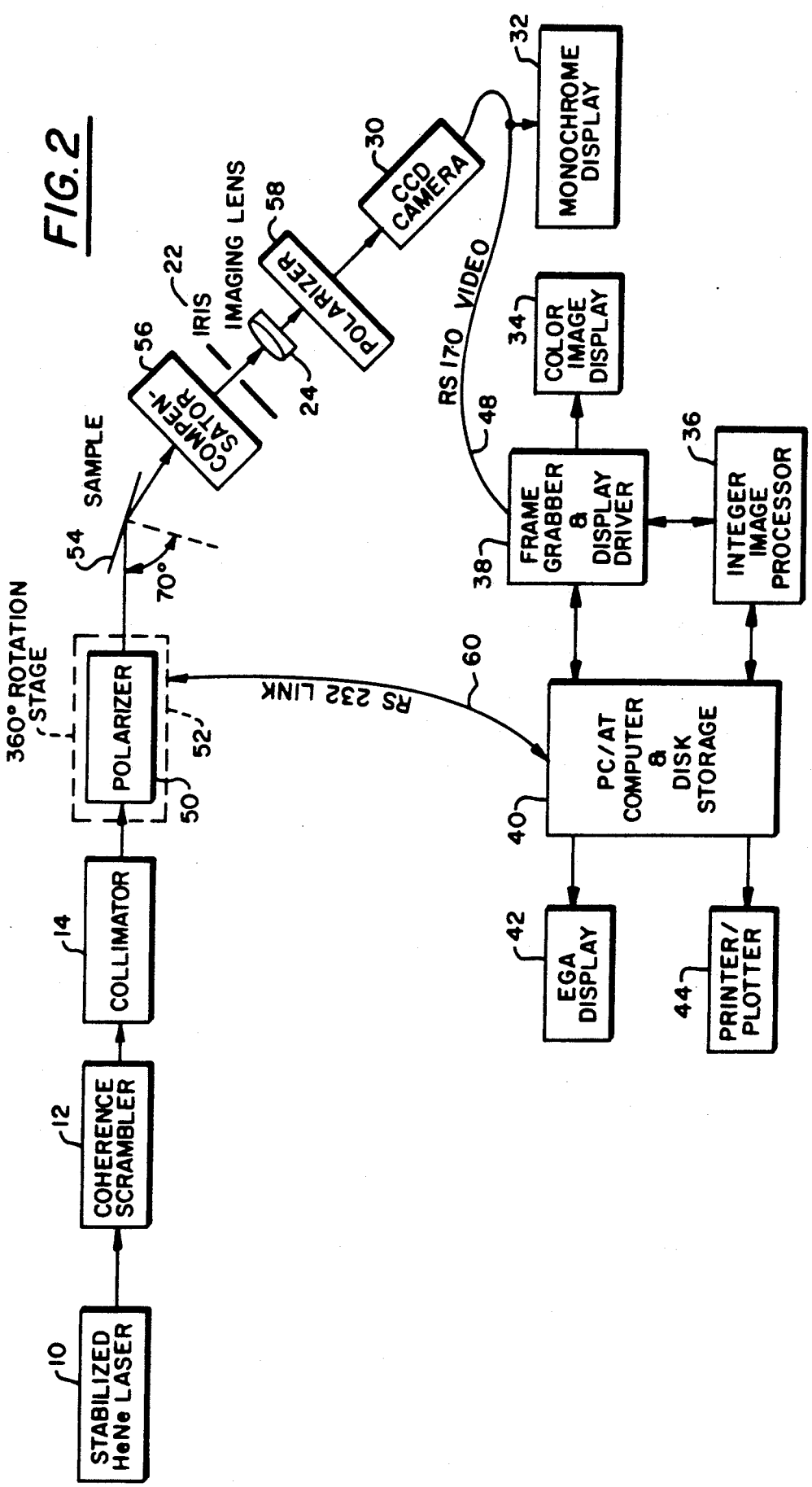

DYNAMIC IMAGING MICROELLIPSOMETRY

FIELD OF THE INVENTION

Ellipsometry is the study of elliptically polarized light resulting from optical reflection. The properties of the reflecting surface can be interpreted from the change in state of polarization caused by reflection. Ellipsometry allows, for electrochemical purposes, surfaces to be examined in any optically transparent medium. Ellipsometry has proven to be an effective method for the examination of thin films, and ellipsometry allows the determination of the thickness and optical properties of thin films.

Two parameters are important to the understanding of ellipsometry. One parameter is the change in relative amplitude of two orthogonal components of the electric field, expressed as the tangent of an angle $\psi$ $$\frac{|E_p|}{|E_s|} = \tan\psi \text{ or } \psi = \tan^{-1}\frac{|E_p|}{|E_s|}$$

where p indicates the vector component parallel to the plane of incidence and s indicates the vector component perpendicular to the plane of incidence. Both $E_s$ and $E_p$ are time varying vector quantities. Because light is considered as time varying, the other parameter relates to the difference of the time-independent phase $\epsilon$ of the two orthogonal components and is expressed as $\Delta$ where $$\epsilon_p - \epsilon_s = \Delta \qquad (2)$$

and the $\epsilon_p$ and $\epsilon_s$ are related to the phase of the respective electric field component.

$$E_{tp} = |E_p|\cos(\omega t + \epsilon_p) \qquad (3)$$

$$E_{ts} = |E_s|\cos(\omega t + \epsilon_s)$$

Knowing the optical constants of a thin film, thickness and refractive index can be determined. Imposing narrower limits on acceptable solutions would often allow the determination of more than two unknowns.

The use of computers has improved the ability to solve the complicated equations relating to ellipsometry and has made ellipsometry an increasingly valuable tool.

BACKGROUND OF THE INVENTION

The importance of thin films in both science and technology has created a need to better understand films. An active area of basic corrosion research is the study of passive film formation and breakdown aimed at improving metallic resistance to attack (K. Sugimoto and S. Matsuda, "Analysis of Passive Films on Austeno-Ferritic Stainless Steel by Microscopic Ellipsometry", *Journal of the Electrochemical Society*, vol. 130, No. 12, December 1983 and K. Sugimoto, S. Matsuda, Y. Ogiwara, and K. Kitamura," Microscopic Ellipsometric Observation of the Change in Passive Film on 18Cr-8Ni Stainless Steel with the initiation of Growth and Pit", *Journal of the Electrochemical Society*, vol. 132, No. 8, August 1985). Processes such as passive film changes during breakdown is one such area where a better understanding is needed. One area in which a better understanding would be useful is in the field of corrosion resistance. Corrosion resistance on many metals results from a thin passive oxide film which forms on a surface and protects the metal substrate. When the passive film layer is destroyed by localized chemical species, such as chloride ions, or mechanical abrasion, corrosion attack can occur.

Ellipsometry has proven to be a standard tool for the measurement of thin film thickness which has been restricted to a limited number of measurements on a surface at low spatial resolution. Up until now it has not been possible to image rapid film changes such as those that occur in an aqueous electrolyte under electrochemical control.

When spatially resolved images of film thickness variations are needed, the beam is focused to a small spot size and scanned over the surface (J. Kruger, "Applications of Ellipsometry to Electrochemistry", *Advances in Electrochemistry and Electrochemical Engineering*, vol. 9, Delahay and Tobias, John Wiley and Sons, New York, 1973; C. L. McBee and J. Kruger, "Events Leading to the Initiation of the Pitting of Iron", Localized Corrosion NACE-3, 1974; and C. L. McBee and J. Kruger, "Ellipsometric-Spectroscopy of Films Formed on Metals in Solution", *Surface Science*, vol. 16, 1969). This procedure produces very accurate ellipsometric results with good spatial resolution but poor temporal resolution due to excessive data acquisition times. By the time the entire area of the specimen had been scanned, the system had undergone serious change. One system available commercially ("Auto Gain Ellipsometers", Bulletin EE, page 13, Gartner Scientific Corp.) specifies an average of four seconds per point. To record a moderately sized image, 100 pixels square, more than eleven hours would be required. Another system ("Optical Sol-gel Coatings: Ellipsometry of Film Formation", A. J. Hurd and C. J. Brinker, *J. Phys. France*, Pre-print) exists which derives useful spatial information by tracking several distinct nulls in a film whose thickness was undergoing change. Because not all of the regions of the film satisfy the null conditions, this system does not yield a complete ellipsometric analysis.

High spatial resolution, finer than 25 microns, along with greatly increased measurement speed is needed to advance the study of rapidly changing thin films.

SUMMARY OF THE INVENTION

The method and apparatus of this invention include a system for imaging ellipsometry based on a polarizer, compensator, specimen, and analyzer used in combination with an imaging lens and mosaic focal plane detector, capable of detecting an area of light whose size is many square pixels reflected from the specimen rather than just a single pixel of reflected light. When spatial variations in imaged surface film parameters exist within the field of view, null ellipsometric techniques are not adequate because multiple simultaneous detectors cannot be uniformly nulled.

To overcome these limitations, a radiometric approach is employed. Radiometric techniques rely upon accurate intensity measurements rather than measuring an optical component angle at which a null intensity is achieved. Using modified radiometric ellipsometry combined with current video and image processing techniques has yielded a flexible system which is capable of meeting the experimental requirements for data acquisition speed and spatial resolution. The radiometric method employed uses the excellent linearity and stability of a charged couple device (CCD) detector to record the light intensity of entire areas at three or more instrument settings as described below. The and ellipsograms are then calculated from the intensity distributions and known instrument settings. The calculations are done by applying a Jones vector and matrix approach (R. M. N. Azzam and N. M. Bashra, *Ellipsometry and Polarized Light*, Elsevier Science Publishers B. V., 1987).

The electric field vector of the light emerging from the analyzer is described by the following matrix equation.

$$E_{AO}^{te} = T_A^{te} R(A) T_S^{xy} R(-C) T_C^{fs} R(C=P) E_{PO}^{te} \quad (4)$$

The superscripts specify each matrix's reference coordinate system and the subscripts specify the optical component represented. The R matrices perform transformations between reference systems. The angles of the polarizer, compensator, and analyzer relative to the X axis are labeled P, C, and A respectively. The individual matrices are defined as follows: normalized electric field at the polarizer output referred to the transmissions-extinction axis is $$E_{PO}^{te} = K_p \begin{bmatrix} 1 \\ 0 \end{bmatrix} \quad (5)$$

waveplate compensator matrix referred to the fast-slow axes $$T_C^{fs} = K_c \begin{bmatrix} 1 & 0 \\ 0 & \rho_c \end{bmatrix} \quad (6)$$

Specimen matrix referred to the x-y axes $$T_S^{xy} = \begin{bmatrix} V_{ex} & 0 \\ 0 & V_{ey} \end{bmatrix} \quad (7)$$

Analyzer (polarizer) matrix referred to the transmission-extinction axes $$T_A^{te} = K_A \begin{bmatrix} 1 & 0 \\ 0 & 0 \end{bmatrix} \quad (8)$$

Reference coordinate system transformation matrix applying an axes rotation by angle $\alpha$ $$R(\alpha) = \begin{bmatrix} \cos\alpha & \sin\alpha \\ -\sin\alpha & \cos\alpha \end{bmatrix} \quad (9)$$

Applying equations 5 through 9 reduce equation 4 to the following scaler relationship $$E_{AO}^{te} = K_p K_A K_c V_{ey} \{\cos A \tan\psi \, e^{j\Delta}[\cos C \cos(P - C) - \rho_c \sin C \sin(P - C)] + \sin A \,[\sin C \cos(P - C) + \rho_c \cos C \sin(P - C)]\} \quad (10)$$

where $$V_{ex}/V_{ey} = \tan\psi \, e^{j\Delta} \quad (11)$$

and where $$j = \sqrt{-1} \quad (12)$$

If the assumption that the compensator is an ideal quarter-waveplate is made with $$\rho_c = e^{-j\pi/2} = -j \quad (13)$$

and setting $$G = K_p K_A K_c |V_{ey}| \quad (14)$$

the intensity of the light emerging from the analyzer is solved for $$I(A) = \quad (15)$$

$$E_{AO}^{te}(E_{AO}^{te})^* = (G^2/2)\,([1 + \cos 2C \cos 2(P - C)]\cos^2 A \times \tan^2\psi + [1 - \cos 2C \cos 2(P - C)]\sin^2 A + [\sin 2C \cos 2(P - C)\cos\Delta - \sin 2(P - C)\sin\Delta]\sin 2A \tan\psi)$$

Notice that equation 15 contains 6 variables. Angles P and C are set to known values and are treated as constants. The analyzer angle A is the control variable which is set to selected positions at which measurements of the intensity are made. There are now three unknowns at each point in the image field: G; the system gain; $\psi$, and $\Delta$. A minimum of three equations are necessary to solve for $\psi$ and $\Delta$. If a larger set of images per ellipsogram are used, measurement error is decreased at the cost of increased acquisition time and larger data storage requirements.

The present invention uses four analyzer positions, though this number can be changed. Using four analyzer settings simplifies the resulting equations and reduces computer calculation time. Images are captured at analyzer settings of 0°, 45°, −45°, and 90°. If these angles are put into equation 15, the result is four dependent equations solvable for $\psi$ and $\Delta$.

$$\psi = \tan^{-1}\left(\sqrt{\frac{1 - \cos 2C \cos 2(P - C)}{1 + \cos 2C \cos 2(P - C)}} \sqrt{\frac{I(0°)}{I(90°)}}\right) \quad (16)$$

$$\Delta = \quad (17)$$

$$\cos^{-1}\left(\frac{I(45°) - I(-45°)}{2\sqrt{I(0°)\,I(90°)}}\right) + \tan^{-1}\{(\sin 2C)^{-1}\tan 2(P - C)\}$$

In the above two equations, neither the attenuation of the optical system nor the input light intensity appears. If the system gain is held constant during the few seconds needed to perform a complete acquisition of four images, no calibration of system gain is required. Though dark signal offset does not appear in equation 15 and must be removed, it is a simple task. Because the terms involving the compensator and polarizer angles are separable from the image intensity terms, any errors in component setting can be removed via calibration using a reference sample.

The PCSA (polarizer, compensator, specimen, analyzer) system was chosen for its superior error performance over a wide range of samples. A computer based error analysis has shown that minimum error occurs in a radiometric ellipsometer when the light reflected from the sample is circularly polarized. Analysis also concluded that a PCSA system can be adjusted to shift the minimum error relative to $\psi$ and $\Delta$ by circularizing the reflected light.

To compute error in and $\psi$ and $\Delta$, the error in the four input intensities was estimated using the Standard Error Formula $$\sigma_{I(A)} = \left( \sum_{i=1}^{n} \left( \frac{\partial I(A)}{\partial x_i} \right)^2 \sigma_{x_i}^2 \right)^{\frac{1}{2}} \quad (18)$$

in which terms for analyzer angle error, detector shot noise, camera electronics noise, A/D quantization noise, and finite linear polarizer extinction ratio magnitude (G. Dahlquist, Å. Bjorck, and N. Anderson, *Numerical Methods*, p. 30, Prentice-Hall, 1974).

After deriving the four intensity error terms using equation 18, the errors $\Delta(\psi)$ and $\Delta(\Delta)$ were calculated using the above results in the maximal error formula, application to non-random errors $$\Delta y \leq \sum_{A} \left| \frac{\partial y}{\partial I(A)} \right| |\Delta I(A)| \quad (19)$$

where I(A) was approximated by the estimate for I(A).

Applying equations 18 and 19 to $\psi$ and $\Delta$ results in a family of curves showing an estimated error bound defining the maximum error magnitude. Assuming a camera with a 60 dB signal-to-noise ratio, eight bit digitization, 0.02° analyzer angle standard deviation and a polarizer extinction ratio of $10^{-5}$ and using a polarizer and compensator both set to 45°, the reflected light's polarization state is directly determined by the sample's ellipsometric parameters. The minimum error can be found at $\Delta = 90°$ and $\psi = 45°$. With $\psi = 45°$, the maximum light intensifies at the detector are found when $\Delta$ approaches 0° or 180°. By making the maximum possible use of the camera's dynamic range, it is possible to minimize ellipsometric error. It is important to have the capability to tune the system so that the available measurement range may be used to best advantage on an arbitrary sample, and to do this requires a polarizer and compensator which can be set to adjust the system for maximum accuracy.

To determine optimized P and C angles in a PCSA system for a given $\psi$ and $\Delta$, the following method is used. The polarization state of the light after reflection is described by the Jones vector $$E_{SO}^{xy} = \begin{bmatrix} V_{ex}[\cos C \cos(P - C) + j \sin C \sin(P - C)] \\ V_{ey}[\sin C \cos(P - C) - j \cos C \sin(P - C)] \end{bmatrix} \quad (20)$$

The ratio of the x vector divided by the y vector is computed, yielding a scaler equation in standard ellipsometric form. This equation represents the reflected light's polarization state which is equated to the desired circular polarization state:

$$e^{j\pi/2} = \tan\psi e^{j\Delta} \left[ \frac{\cos C \cos(P - C) + j \sin C \sin(P - C)}{\sin C \cos(P - C) - j \cos C \sin(P - C)} \right] \quad (21)$$

This equation is next split into two separate equalities, one representing the magnitude term and the other the phase. The magnitude equation is reduced to the following convenient form:

$$P = \frac{1}{2} \cos^{-1} \left[ \frac{\cos 2\psi}{\cos 2C} \right] \quad (22)$$

and the phase term is reduced to $$P = -\frac{1}{2}\tan^{-1}[\sin 2C \tan(\Delta - \pi/2)] + C \quad (23)$$

By inputting C angles, the P angle can be computed. The solution yielding circular polarization is found at the intersection point of the two curves.

BRIEF DESCRIPTIONS OF THE DRAWINGS

The advantages of the present invention may be better understood from studying the following detailed description of the presently preferred exemplary embodiment together with the drawings in which:

FIG. 2 is a block diagram of a second embodiment according to the present invention;

DETAILED DESCRIPTION OF THE PRESENTLY PREFERRED EXEMPLARY EMBODIMENT

Figure 1:
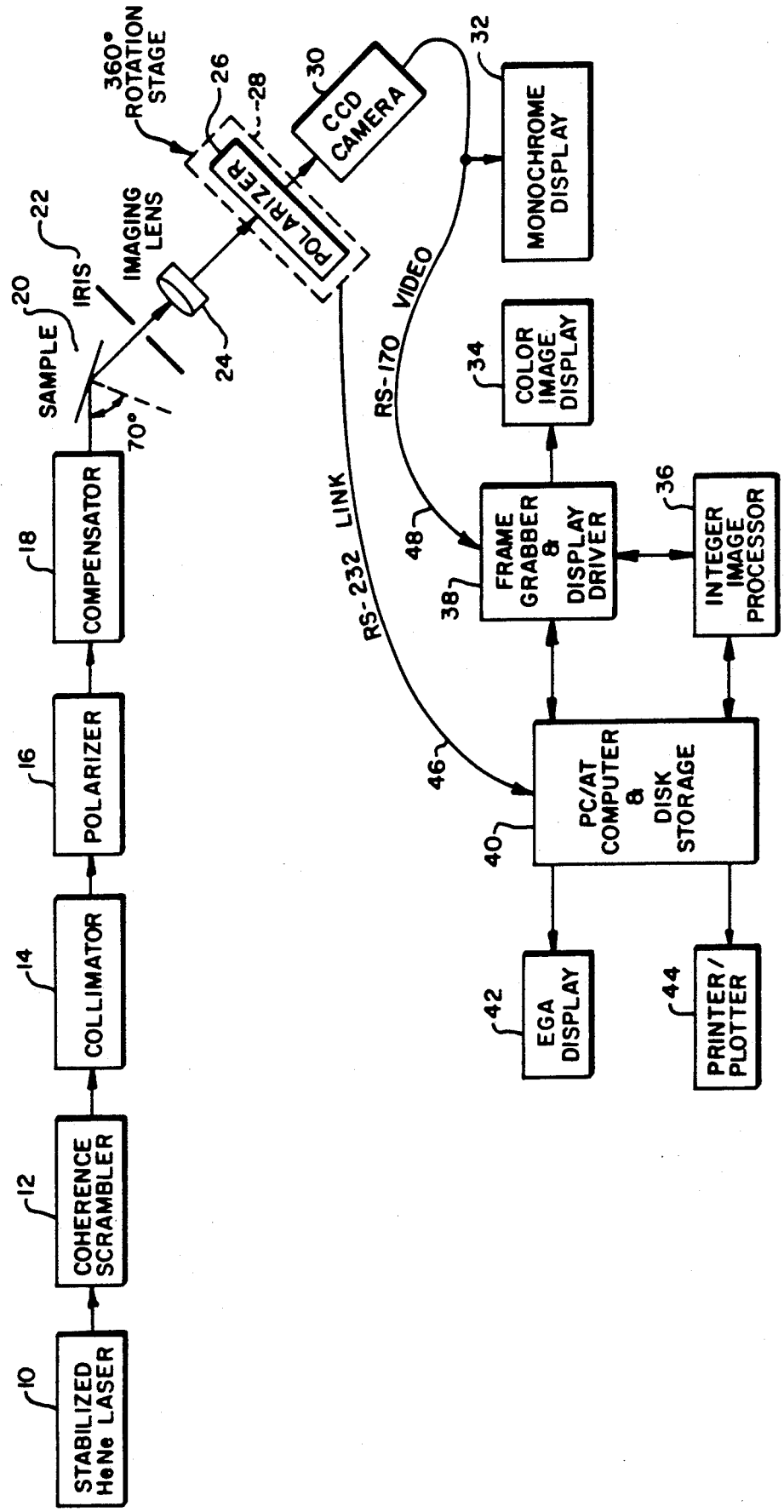
FIG. 1 is a block diagram of a first embodiment according to the present invention.
Figure 3A:
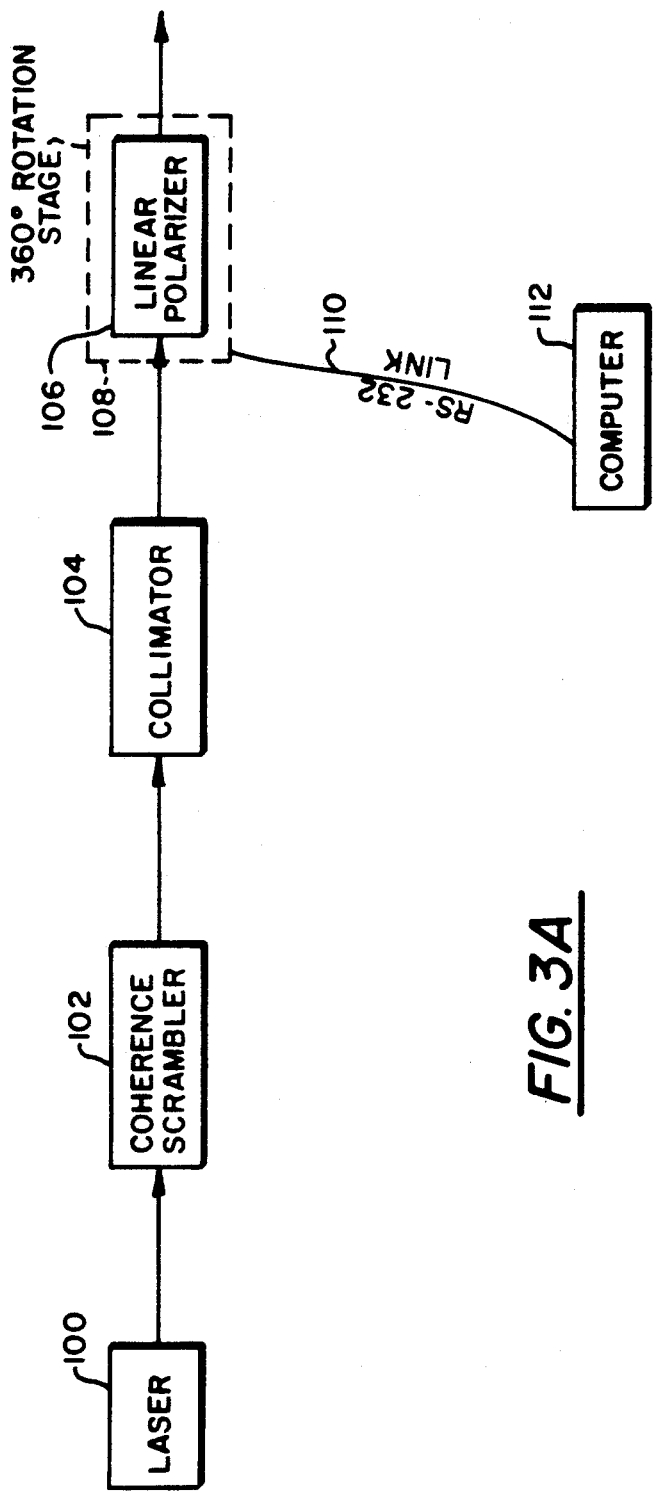
FIG. 3A is a block diagram of a useful polarization rotation method.
Figure 3B:
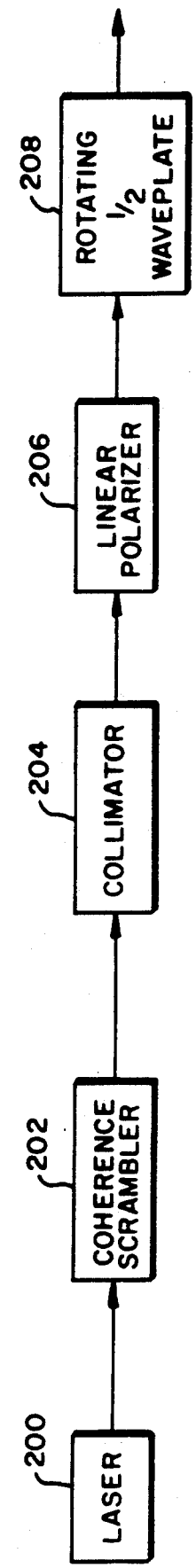
FIG. 3B is a block diagram of a second useful polarization rotation method.

FIG. 1 is a block diagram of the apparatus configuration according to the present invention. The light source used is a Helium-Neon (HeNe) laser 10 with active stabilization. The laser 10 provides a bright, highly monochromatic, coherent, intensity stable source. The active stabilization maintains constant beam intensity throughout the measurement cycle. A coherence scrambler 12 is needed to reduce beam coherence, thereby reducing any diffraction and interference effects in the image caused by dust or optical imperfections. The coherence scrambler could be a piece of equipment such as a ground glass disk spinning at approximately 1800 rpm which is used in the first and second embodiments. It is also possible to replace the laser and coherence scrambler with a high brightness light emitting diode (LED).

A collimator 14 then collimates the beam which passes through a polarizer 16; in the preferred embodiment, the polarizer 16 is a Glan-Thompson polarizer, a birefringent polarizer constructed from two calcite prisms cemented together. The beam emerging from the polarizer 16 then travels through a compensator 10, which is a quarter waveplate compensator in the present invention. Both the polarizer 16 and compensator 18 are set in manual rotation stages which can be set to a fixed positions for each specimen.

The specimen 20 is mounted on a translation-rotation stage which is set for 70° angle of incidence. After the beam reflects from the specimen 20, it passes through an iris aperture 22 to an imaging lens 24. The imaging lens 24 of the preferred embodiment has an adjustable aperture stop for depth of field control when viewing at the 70° angle of incidence. Prior to each measurement, the analyzer 26 can be positioned using the computer controlled 360° rotation stage 28 to which it is attached. The rotation stage 28 is connected to the computer and disk storage unit 40 by a cable 46. The light beam passing through the analyzer 26 forms an image on a mosaic focal plane detector which is a Charge Coupled Device camera 30. The camera 30 is capable of sensing an area of reflected light many pixels on a side instead of having to the same area and thereby losing any temporal resolution. A monochromatic display 32 is connected directly to the camera 30 to monitor the camera view.

To control system operation, capture and process images, and display the results, a computer and disk storage unit 40 with certain attached peripherals is used. The computer unit 40 used is one such as an IBM PC/AT. A High Resolution Frame Grabber board 38 with 8 bit resolution 38 and an auxiliary frame processor 36 perform all basic integer arithmetic image processing and display. In the preferred embodiment the framegrabber board 38 used was a Data Translation DT-2851 High Resolution Frame Grabber and the frame processor board 36 was a Data Translation DT-2858 Auxiliary Frame Processor board. A high resolution color image display 34 displays the image sent from the frame grabber 38 and image processor 36. In the preferred embodiment, the computer 40 functions on a STSC APL*-PLUS system for general control, analysis, and graphics or a FORTRAN system for speed. A color EGA display 42 and a graphics printer/plotter 44 provide line and surface plots for quantitative ellipsometric analysis. Pseudo-colored ellipsograms and raw image displays are used for qualitative analysis and image feature identification.

The major goals of the DIM design were to obtain high spatial resolution and fast data acquisition times. The DIM system of the first embodiment achieves the spatial resolution required by digitizing 480 video lines with 512 pixels on each line. This area would have taken many hours to scan with older data acquisition techniques but now takes less than a minute. The actual spatial resolution is determined by the magnification factor for the imaging lens with some degradation along the X axis caused by defocusing due to the 70° viewing angle. A five micron resolution has been demonstrated using a magnification factor of roughly eight. A factor limiting magnification is the need for sufficient light intensity for the fixed dynamic range video radiometric measurements, which limits the maximum usable magnification. Increasing the light source brightness would widen the magnification range until the limit caused by partially coherent diffraction is reached.

Temporal resolution is somewhat more involved. The cable 48 carrying information to the frame-grabber operates at an image frame rate of 30 frames per second. With four frames per ellipsogram needed, the maximum speed per ellipsogram would be 0.133 seconds. This estimate does not allow for time to rotate the analyzer 45° between frames. The stepper motion on the rotation stage operates at only 10° per second speed, though faster motors are available. Further time is lost because it is necessary to increase optical integration time by averaging frames when acquiring intensity images in order to reduce shot and camera noise. The Date Translation system is limited to roughly 5.5 frames per second. Because the prototype system's image processor contains only two storage frames, images must be stored during the acquisition cycle. The analyzer rotation is done during the storage process and is not a limiting factor in this case. When the four images are recorded at uniform time intervals with 16 video frames averaged per image, 55 seconds are needed.

FIG. 2 is a block diagram of the second embodiment of the present invention. Instead of using a PCSA system, a PSCA, polarizer 50, specimen 54, compensation 56, analyzer 58, system is used. This variation has the polarizer 50 rather than the analyzer 58 as the active element. The polarizer 50 is set on a 360° rotation stage 52 controlled by the computer 40. When rotating the polarizer 50 rather than the analyzer 58, two main advantages exist. First, the birefringent polarizing prisms cause a beam offset from the optical axis with the magnitude depending on the incidence angle and polarization state. When the analyzer 58 rotates, error is introduced in that the analyzer rotation causes a translation in the image. Secondly, when the analyzer 58 rotates near an image plane, any dust or imperfections may be blurred but visible and shifted in location from frame to frame, causing imperfections in the ellipsogram. The same beam shifts occur in the rotating polarizer 50, but since this is prior to reflection from the sample no images shifts result and the major concern is maintaining a constant intensity over the field of view. Placing the rotating polarizer 50 first in the optical configuration allows for polarization modulation techniques that might otherwise alter the image if used at the analyzer 58.

The same light emitter is used and also the same computer and video equipment. The CCD camera capable of recording areas rather than single pixels is still used. In the second embodiment, the computer 40 is linked to the rotation stage 52 by a RS-232 link 60. Recent experimentation has shown that a high brightness light emitting diode has some advantages over using a laser source.

Two polarization rotation methods have been used in the dynamic imaging microellipsometer. The first has been previously discussed in the second embodiment. A laser 100 is passed through a coherence scrambler, a rotating ground glass disk, and then through a collimating lens 104. The beam is then passed through a linear polarizer 106 mounted on a rotation stage 108 linked by a RS-232 link 110 to a controlling computer 112.

The second polarization rotation method has a laser 200 projecting a beam on a coherence scrambler 202, a rotating ground glass disk, then to a collimating lens 204. From there, the beam passes through a linear polarizer 206 and then a rotating $\frac{1}{2}$ waveplate 208. This arrangement has three advantages. First, the $\frac{1}{2}$ waveplate rotates linear polarizations by a factor of two, thus, it is required to travel only $\frac{1}{2}$ the rotation of a linear polarizer, speeding the ellipsogram capture. The second advantage is that with a linearly polarized laser, more efficient use of the light is obtained. Possibly most important is that a rotating $\frac{1}{2}$ waveplate ascertains constant illumination intensity.

Figure 4:
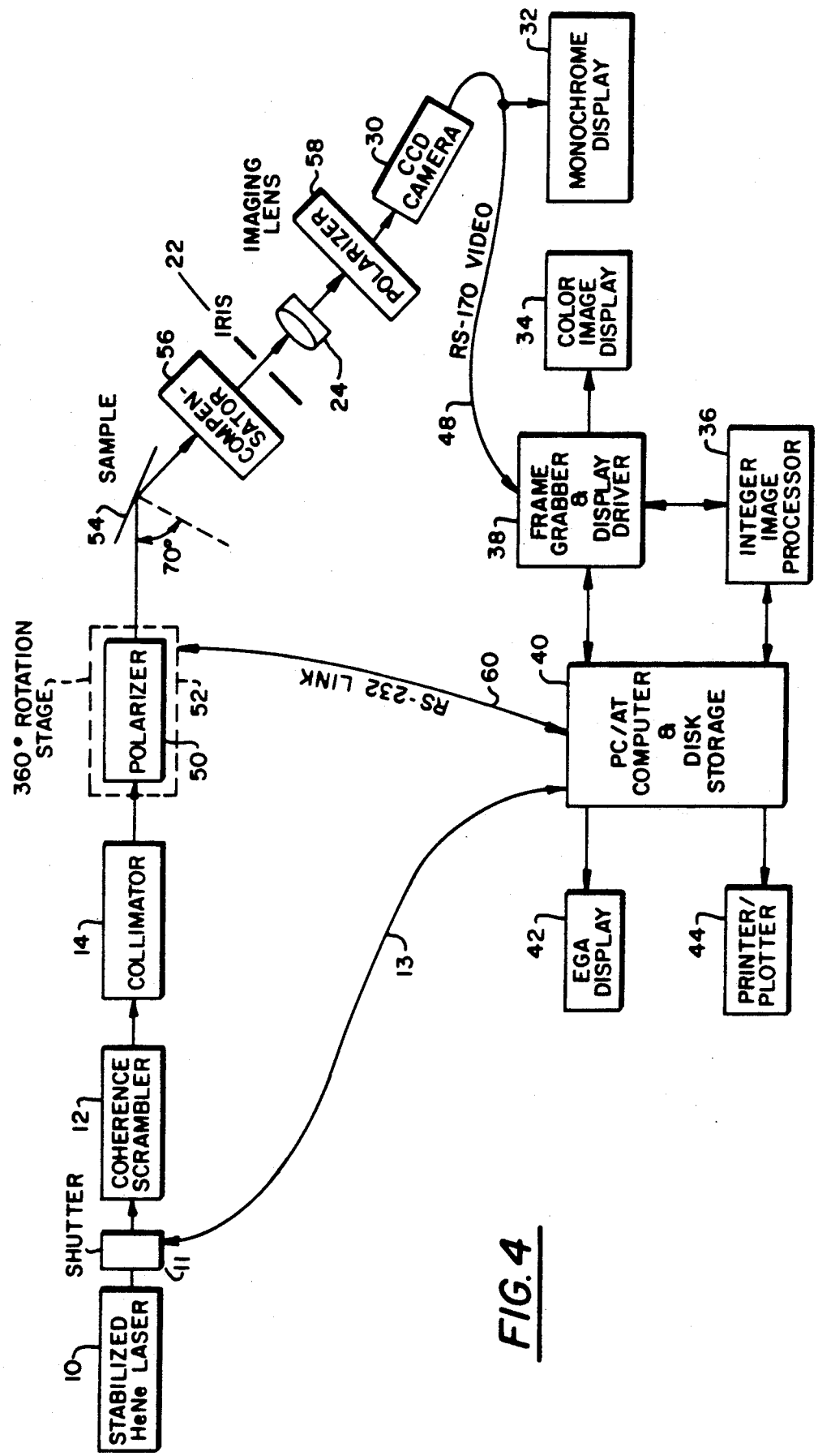
FIG. 4 is a block diagram of the invention with an automated shutter in use.

FIG. 4 is a block diagram of an embodiment of the invention with a shutter introduced. The shutter 11 is positioned right after the light source 10 and is connected to computer 40 by link 13 so as to be under computer control. The shutter 11 is closed to form a dark field image and is then opened to form a lighted image. The dark image is subtracted from the lighted image for the process of dark signal removement.

While the present invention has been described in connection with what is presently considered to be the most practical and preferred embodiments, it is to be understood that the invention is not limited to the disclosed embodiments, but is intended to cover various modifications and equivalent arrangements included within the scope of the appended claims. For example, the temporal resolution could be improved using image processors that can perform the averaging at the full video frame rate. Alternative light sources can be used. For faster DIM operation, non-mechanical polarization rotation and line scan or high frame rate CCD cameras could be used. Optical integration time can be reduced by using state of the art cooled CCD cameras with deeper pixel well depths and low camera noise levels. Averaging groups of pixels will further increase the effective well depth though it will sacrifice spatial resolution. With an increased signal dynamic range, 10 or 12 bit digitization can be used to reduce the quantization noise and increase ellipsometric resolution with fewer frames averaged. Further time resolution can be achieved for samples with small variations in ellipsometric parameters. Another possibility is using large, high speed data storage.

What is claimed is:

1. A dynamic imaging microellipsometry apparatus, developed for high spatial resolution and high speed data acquisition, which comprises:
   means providing a beam of light which illuminates an area on a selected surface of a specimen and providing a reflected beam;
   means for polarizing said reflected beam; means for rotating said polarizing means to alter at least one characteristic of an image;
   a detector means for receiving said reflected beam of light from said specimen, said detector means being capable of detecting light reflected over substantially the entirety of said surface of said specimen illuminated by said beam; and
   computer and video apparatus for receiving and displaying the image provided by the reflected beam.

2. The apparatus as in claim 1 wherein said means providing a beam of light includes a light emitting member capable of providing a beam of constant intensity throughout a measurement cycle.

3. The apparatus as in claim 2 further comprising;
   an optical member to reduce beam coherence so as to reduce affects of diffraction or interference caused by dust or optical imperfections;
   a collimator; and
   a polarizer capable of being positioned for each case;
   a compensator for altering the phase of said beam of light and able to be rotated for each case; and
   means for mounting said specimen at an angle such that the incident light strikes said specimen with said angle being greater than 0° and less than 90°.

4. The apparatus as in claim 2 further comprising:
   an optical member to reduce beam coherence so as to reduce affects of diffraction or interference caused by dust or optical imperfections;
   a collimator;
   a polarizer capable of being rotated by computer control so as to produce different images for each case;
   means for mounting a specimen at an angle such that the incident light strikes said sample with said angle being greater than 0° and less than 90°; and
   a compensator through which the reflected beam passes.

5. Apparatus as in claim 3 or 4 wherein said optical member to reduce beam coherence is a spinning ground glass disk.

6. Apparatus as in claim 3 or 4 wherein means for mounting said specimen is a translation-rotation support set for a 70° angle of incidence.

7. The apparatus as in claim 3 or 4 further comprising a shutter controlled by said computer apparatus positioned after said light emitting member.

8. Apparatus as in claim 3 wherein said polarizer is a Glan-Thompson polarizer and said compensator is a quarter waveplate, each set in a manual rotation stage set to fixed positions for each specimen.

9. Apparatus in claim 1 wherein said means for polarizing is mounted on a 360° rotation support control by said computer to produce different images of said specimen.

10. Apparatus as in claim 1 wherein said mosaic focal plane detector means is a charge coupled device camera.

11. Apparatus as in claim 1 wherein said computer and video apparatus includes peripherals including;
    a high resolution frame grabber with at least 8 bit resolution;
    an auxiliary frame processor board;
    a monochromatic display connected to the output of said detector means so as to monitor the view of said detector means;
    a high resolution color display to assist in evaluation of image processor output; and
    a color EGA display and graphics printer which provide line and surface plots for quantitative ellipsometric analysis.

12. A method of forming images of thin films specimens using a dynamic imaging microellipsometry system comprising the steps of:
    providing a beam of light of constant intensity which illuminates an area on a selected surface of said specimen;
    reflecting said beam of light off said specimen and directing a reflected beam so as to pass through polarizing means, said polarizing means being rotatable so as to alter at least one characteristic of an image;
    detecting said reflected beam using a detector means, said detecting means being capable of detecting light reflected over substantially the entirety of said surface;
    using computer and video apparatus to analyze and display the intensity pattern of said detected beam.

13. A method as in claim 12 further including the step of using a helium-neon laser to provide said beam of light.

14. A method as in claim 12 further comprising the step of mounting said specimen so that said beam of light strikes said sample at an angle, said angle being greater than 0° and less than 90°.

15. A method as in claim 12 further comprising using a charged coupled device camera as said detecting means.

* * * * *